(12) United States Patent
Jourdan et al.

(10) Patent No.: US 10,045,999 B2
(45) Date of Patent: *Aug. 14, 2018

(54) NUTRITIONAL COMPOSITION FOR THE STIMULATION OF MUSCLE PROTEIN SYNTHESIS

(71) Applicant: N. V. Nutricia, Zoetermeer (NL)

(72) Inventors: Marion-Eve Adeline Jourdan, Utrecht (NL); Yvette Charlotte Luiking, Utrecht (NL); George Verlaan, Utrecht (NL); Sovianne Ter Borg, Utrecht (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/750,061

(22) Filed: Jun. 25, 2015

(65) Prior Publication Data
US 2015/0290223 A1    Oct. 15, 2015

Related U.S. Application Data

(63) Continuation of application No. 13/808,630, filed as application No. PCT/NL2011/050488 on Jul. 6, 2011, which is a continuation-in-part of application No. PCT/NL2010/050436, filed on Jul. 7, 2010.

(51) Int. Cl.
| | | |
|---|---|---|
| *A23L 33/175* | (2016.01) |
| *A23L 33/155* | (2016.01) |
| *A23L 33/19* | (2016.01) |
| *A23L 33/21* | (2016.01) |
| *A61K 31/593* | (2006.01) |
| *A61K 31/198* | (2006.01) |
| *A61K 31/592* | (2006.01) |
| *A61K 31/59* | (2006.01) |
| *A23L 33/00* | (2016.01) |

(52) U.S. Cl.
CPC .......... *A61K 31/593* (2013.01); *A23L 33/155* (2016.08); *A23L 33/175* (2016.08); *A23L 33/40* (2016.08); *A61K 31/198* (2013.01); *A61K 31/59* (2013.01); *A61K 31/592* (2013.01); *A23V 2002/00* (2013.01); *A23V 2200/316* (2013.01); *A23V 2250/0614* (2013.01); *A23V 2250/0628* (2013.01); *A23V 2250/306* (2013.01); *A23V 2250/71* (2013.01)

(58) Field of Classification Search
USPC ........................................................ 514/176
See application file for complete search history.

(56) References Cited

U.S. PATENT DOCUMENTS

| | | |
|---|---|---|
| 2004/0122097 A1 | 6/2004 | Verlaan et al. |
| 2006/0275506 A1 | 12/2006 | Fisher et al. |
| 2009/0042770 A1 | 2/2009 | Bastian et al. |
| 2009/0220637 A1 | 9/2009 | Roessle |
| 2010/0124587 A1 | 5/2010 | Heuer et al. |

FOREIGN PATENT DOCUMENTS

| | | |
|---|---|---|
| EP | 1330957 A2 | 7/2003 |
| EP | 1712140 A1 | 10/2006 |
| EP | 2036552 A1 | 3/2009 |
| JP | 2008237070 A | 10/2008 |
| WO | 01/60378 A2 | 8/2001 |
| WO | WO-2004/026294 A1 | 4/2004 |
| WO | 2005/039597 A2 | 5/2005 |
| WO | WO-2006/026458 A2 | 3/2006 |
| WO | 2006/062273 A1 | 6/2006 |
| WO | WO-2007/043870 A1 | 4/2007 |
| WO | 2007/057748 A2 | 5/2007 |
| WO | 2008/049984 A2 | 5/2008 |
| WO | 2008/115563 A1 | 9/2008 |
| WO | 2009/113858 A1 | 9/2009 |
| WO | 2010/143939 A1 | 12/2010 |
| WO | WO-2010/143947 A1 | 12/2010 |
| WO | WO-2011/011252 A1 | 1/2011 |
| WO | 2012/005582 A1 | 1/2012 |
| WO | WO-2012/024611 A1 | 2/2012 |
| WO | WO-2012/091571 A2 | 7/2012 |

OTHER PUBLICATIONS

NIH Office of Dietary Supplements (Vitamin D, 2009, pp. 1-11) (hereinafter NIH).*
Bartali, Benedetta, et al.,"Low Nutrient is an Essential Component of Frailty in Older Persons," Journal of Gerontology: Medical Sciences, 2006, pp. 589-593, vol. 61A, No. 6, The Gerontological Society of America.
Bendahan, D., et al."Citrulline/malate promotes aerobic energy production in human exercising muscle," Br J Sports Med, 2002, pp. 282-289, vol. 36, British Association of Sport and Exercise Medicine in association with the National Sports Medicine Institute.
Bouillon, Roger, et al.,"Vitamin D Deficiency," The New England Journal of Medicine, 2007, pp. 1980-1982, vol. 357, No. 19, Massachusetts Medical Society.
Cuthbertson, Daniel, et al.,"Anabolic signaling deficits underlie amino acid resistance of wasting, aging muscle," The FASEB Journal, 2004, pp. 1-22.
Dardevet, Dominique, et al.,"Stimulation of In Vitro Rat Muscle Protein Synthesis by Leucine Decreases with Age," The Journal of Nutrition, 2000, pp. 2630-2635, vol. 130, American Society for Nutritional Sciences.
Guillet, Christelle, et al., Impaired anabolic response of muscle protein synthesis is associated with S6K1 dysregulation in elderly humans, The FASEB Journal, 2004, pp. 1-16.

(Continued)

*Primary Examiner* — Kathrien A Cruz (74) *Attorney, Agent, or Firm* — Gilberto M. Villacorta; Sunit Talapatra; Foley & Lardner LLP (57) ABSTRACT

The invention relates to the use of an anabolic amino acid derivative stimulus acting in combination with vitamin D for the manufacture of a medicament or nutritional composition for the prevention and/or treatment of a loss of any one of muscle mass, muscle strength, muscle function, and physical function, or any combination thereof, in a mammal.

13 Claims, 1 Drawing Sheet

(56) References Cited

OTHER PUBLICATIONS

Holick, Michael F., "Vitamin D Deficiency," The New England Journal of Medicine, 2007, pp. 266-281, vol. 357, No. 3, Massachusetts Medical Society.
Katsanos, Christos S., "Aging is associated with diminished accretion of muscle proteins after the ingestion of a small bolus of essential amino acids," The American Journal of Clinical Nutrition, 2005, pp. 1065-1073, vol. 82, American Society for Nutrition.
Koopman et al ("Combined ingestion of protein and free leucine with carbohydrate increases postexercise muscle protein synthesis in vivo in male subjects" (2004) Am J Physiol Endocrinol Metab 288: E645-E653).
Lesser, Stephanie, et al., "Nutritional Situation of the Elderly in Eastern/Baltic and Central/Western Europe—The AgeingNutrition Project," Annals of Nutrition & Metabolism, 2008, pp. 62-71, vol. 52, suppl. 1, S. Karger AG, Basel.
Lips, P., "Vitamin D status and nutrition in Europe and Asia," Journal of Steroid Biochemistry & Molecular Biology, 2007, pp. 620-625, vol. 103, Elsevier Ltd.
Marzani, Barbara, et al., "Antioxidant Supplementation Restores Defective Leucine Stimulation of Protein Synthesis in Skeletal Muscle from Old Rats," The Journal of Nutrition, 2008, pp. 2205-2211, vol. 138, American Society for Nutrition.
Morley, John E., et al., "Nutritional Recommendations for the Management of Sarcopenia," J. Am. Med. Dir. Assoc., 2010, pp. 391-396, vol. 11, American Medical Directors Association.
Perez-Guisado, Joaquin, et al.,Citrulline Malate Enhances Athletic Anaerobic Performance and Relieves Muscle Soreness, Journal of Strength and Conditioning Research, 2010, vol. 24, No. 5, National Strength and Conditioning Association.
Pfeifer, M., et al., "Vitamin D and Muscle Function," Osteoporosis International, 2002, pp. 187-194, vol. 13, International Osteoporosis Foundation and National Osteoporosis Foundation.
Rolland, Y., et al., "Sarcopenia: its assessment, etiology, pathogenesis, consequences and future perspectives," The Journal of Nutrition, Health & Aging, 2008, pp. 433-450, vol. 12, No. 7.
Semba, Richard, D., "Low serum micronutrient concentrations predict frailty among older women living in the community," Journal of Gerontology: Medical Sciences, 2006, pp. 594-599, vol. 61A, No. 6, The Gerontological Society of America.
Seshadri, Sudha, et al., "Plasma homocysteine as a risk factor for dementia and alzheimer's disease," The New England Journal of Medicine, 2002, pp. 476-483, vol. 346, No. 7, Massachusetts Medical Society.
Siddiqui (Dietary Intervention with Vitamin D, Calcium and Whey Protein reduced Fat mass and Increased Lean Mass in Rats, Nutr Res, 2008; 28(11 ); pp. 783-790).
Van Laere, Katrien M., "Degradation of Structurally Different Non-Digestible Oligosaccharides by Intestinal Bacteria: Glycosylhydrolases of Bifidobacterium adolescentis," PHD-thesis 2000, pp. 1-152, Wageningen Agricultural University, Wageningen, The Netherlands.
Visser, Marjolein, et al., "Low Vitamin D and High Parathyroid Hormone Levels as Determinants of Loss of Muscle Strength and Muscle Mass (Sarcopenia): The Longitudinal Aging Study Amsterdam," The Journal of Clinical Endocrinology & Metabolism, 2003, pp. 5766-5772, vol. 88, No. 12, The Endocrine Society.
Volek ("Leucine triggers muscle growth" Nutrition Express. downloaded from http://www.nutritionexpress.com/article+index/protein/showarticle.aspx?id=807 on Oct. 18, 2013).
Wicherts, Ilse S., et al., "Vitamin D status predicts physical performance and its decline in older persons," The Journal of Clinical Endocrinology & Metabolism, 2007, pp. 2058-2065, vol. 92, No. 6, The Endocrine Society.
World Health Organization,"Keep fit for life: Meeting the nutritional needs of older persons," 2002, 1-75.
Zittermann, A.,"The estimated benefits of vitamin D for Germany," Mol. Nutr. Food Res., 2010, pp. 1-8, vol. 54, Wiley-VCH Verlag GmbH & Co.
Jarosz et al., "Sarcopenic Obesity: An emerging cause of frailty in older adults", Geriatric Nursing, Jan. 2009, vol. 30, No. I, pp. 64-70.
Villareal et al., "Obesity in older adults: technical review and position statement of the American Society for nutrition and NAASO, The Obesity Society", Obesity Research, Nov. 2005, vol. 13, No. 11, pp. 1849-1863.
Ames et al., "Mineral and vitamin deficiencies can accelerate the mitochondrial decay of aging", Molecular Aspects of Medicine, 2005, vol. 26, pp. 363-378.
Anthony et al., "Leucine stimulates translation initiation in skeletal muscle of postabsorptive rats via a rapamycin-sensitive pathway", The Journal of Nutrition, 2000, vol. 130, pp. 2413-2419.
Bauer et al., "Sarcopenia in nursing home residents", J. Am. Med. Dir. Assoc., 2008, vol. 9, pp. 545-551.
Birge et al., "25-Hydroxycholecalciferol stimulation of muscle metabolism", The Journal of Clinical Investigation, Nov. 1975, vol. 56, pp. 1100-1107.
Bischoff-Ferrari et al., "Effect of vitamin D on Falls: A meta-analysis", JAMA, Apr. 2004, vol. 291, No. 16, pp. 1999-2006.
Dawson-Hughes, "Serum 25-hydroxyvitamin D and functional outcomes in the elderly", The American Journal of Clinical Nutrition, 2008, vol. 88(suppl), pp. 537S-540S.
Dietary Reference Intakes for Japanese (2005), Ministry of Health, Labor and Welfare, Japan, p. 83.
Directive 2002/46/EC of the European Parliament and of the Council, Article 4 & Annex, Jun. 2002.
Holick, "Resurrection of vitamin D deficiency and rickets", The Journal of Clinical Investigation, Aug. 2006, vol. 116, No. 8, pp. 2062-2072.
Katsanos et al., "A high proportion of leucine is required for optimal stimulation of the rate of muscle protein synthesis by essential amino acids in the elderly", Am. J. Physiol. Endocrinol. Metab., 2006, vol. 291, pp. E381-E387.
Leterme et al., "Amino acid composition of pea (*Pisum sativum*) proteins and protein profile of pea flour", J. Sci. Food Agric., 1990, vol. 53, pp. 107-110.
Montero-Odasso et al., "Vitamin D in the aging musculoskeletal system: An authentic strength preserving hormone", Molecular Aspects of Medicine, 2005, vol. 26, pp. 203-219.
Paddon-Jones et al., "Differential stimulation of muscle protein synthesis in elderly humans following isocaloric ingestion of amino acids of whey protein", Experimental Gerontology, 2006, vol. 41, pp. 215-219.
Rieu et al., "Leucine supplementation improves muscle protein synthesis in elderly men independently of hyperaminoacidaemia", J. Physiol., 2006, vol. 575.1, pp. 305-315.
Salles et al., "1,25(OH)2-vitamin D3 enhances the stimulating effect of leucine and insulin on protein synthesis rate through Akt/PKB and mTOR mediated pathways in murine C2C12 skeletal myotubes", Mol. Nutr. Food Res., 2013, vol. 57, pp. 2137-2146.
Shen et al., "Insulin and IGF-I stimulate the formation of the eukaryotic initiation factor 4F complex and protein synthesis in C2C12 myotubes independent of availability of external amino acids", Journal of Endocrinology, 2005, vol. 185, pp. 275-289.
Smith et al., "Measurement of human mixed muscle protein fractional synthesis rate depends on the choice of amino acid tracer", Am. J. Physiol. Endocrinol. Metab., 2007, vol. 296, pp. E666-E671.
Thompson et al., "Milk proteins: from expression to food", Food Science and Technology, International Series, Academic Press, 2009, 5 pgs.

\* cited by examiner

NUTRITIONAL COMPOSITION FOR THE STIMULATION OF MUSCLE PROTEIN SYNTHESIS

RELATED APPLICATION DATA

This application is a continuation application which claims priority to U.S. patent application Ser. No. 13/808,630, filed on Feb. 14, 2013, which is a National Stage Application under 35 U.S.C. 371 of co-pending PCT application PCT/NL2011/050488 designating the United States and filed Jul. 6, 2011; which claims the benefit of PCT application PCT/NL2010/040436 and filed Jul. 7, 2010 each of which are hereby incorporated by reference in their entireties.

FIELD OF THE INVENTION

The present invention relates to the use of an anabolic amino acid derivative stimulus acting in combination with vitamin D for the prevention and/or treatment of a loss of any one of muscle mass, muscle strength, muscle function, and physical function, or any combination thereof, in a mammal, especially an adult mammal, as well as to specific nutritional compositions suitable for stimulating muscle protein synthesis in a mammal, especially an adult mammal.

BACKGROUND OF THE INVENTION

Sarcopenia defines the loss of muscle mass, strength and function occurring during aging [1]. Muscle mass loss starts from the age of 30 years at a rate of 3-8% per decade and accelerates from 60 years of age. This loss reaches up to 35-40% in elderly over 70, and hence, sarcopenia is especially prominent in elderly.

Muscle mass preservation can only be achieved through an adequate stimulation of protein synthesis and/or inhibition of proteolysis. Several factors contribute to muscle protein synthesis among which the most important is the availability of amino acids (serving as building blocks for the newly synthesized proteins) and the activation signal generated by anabolic amino acids or anabolic amino acids derivative (e.g. citrulline, leucine, essential amino acids (EAA), and creatine).

However, protein intake is decreased in elderly, which leads to inadequate postprandial availability of amino acids. Furthermore, aging is characterized by a decreased muscle sensitivity to the anabolic effect of essential amino acids, especially leucine [2, 3]. This lesser responsiveness to leucine is associated with a decrease in the activation of intracellular pathways controlling muscle protein synthesis [4, 5]. Hence, to counteract the deleterious effect of aging on muscle protein synthesis, it is necessary to simultaneously target the bioavailability of amino acids, especially essential amino acids, by increasing the intake of high-quality protein (rich in essential amino acids, especially leucine), and the muscle response to anabolic amino acids by improving muscle sensitivity to these amino acids.

Of interest, aging is also characterized by a high prevalence of vitamin D deficiency (serum vitamin D levels below 25-50 nmol/L) and insufficiency (serum vitamin D levels below 75 nmol/L) [6, 7]. Low serum 25-(OH)D concentrations are associated with an increased risk of sarcopenia in elderly [8].

In the future, vitamin D deficiency could become a major health problem: only recently it was stated [9] that between 40 and 45 percent of the German population could be vitamin D insufficient, with an additional 15 to 30 percent deficient, thereby putting them at risk at a variety of health problems. In addition, current recommendations of daily intake of vitamin D are of 5 micrograms for adults under 50 years old, and 10 micrograms for adults older than 50 years and are not adequate to ensure vitamin D sufficiency (serum vitamin D levels equal or above 75 nmol/L) in the general population. Hence, there is a need to significantly increase these recommendations (at least to double them) and preferably to raise them to a daily intake of 25 micrograms or more depending on gender, age, activity level, and other factors.

Vitamin D deficiency in adults is reported to precipitate or exacerbate osteopenia, osteoporosis, muscle weakness, sarcopenia [11], loss of physical function, fractures, common cancers, autoimmune diseases, infectious diseases and cardiovascular diseases. There is also some evidence that vitamin D may reduce the incidence of several types of cancer and type-1 diabetes.

The science supporting the action of vitamin D on muscle strength, as well as the vitamin's role in immune health, is sufficiently robust to have merited a positive opinion from the European Food Safety Authority's (EFSA) Panel on Dietetic Products, Nutrition and Allergies (NDA) [10].

BACKGROUND PRIOR ART

EP 1 712 140 B1 (Larena, 18 Dec. 2006) discloses a composition intended for the prevention and/or treatment fragility syndrome in elderly subjects and sarcopenia, comprising a large number of components, among which vitamin D (with a maximum of 20 μg) and natural proteins, such as whey, rich in branched chain amino acids (among which leucine). The composition does not contain free leucine, carbohydrates or fat.

WO2006/062273 (Kim, 15 Jun. 2006) teaches a health supplement food essentially consisting of free branched amino acids (among which leucine), and a number of anti-oxidants, among which vitamine D3, said to assist in the absorption and the metabolism of branched amino acids for enhancing instant impact power under anaerobic conditions (for sportsmen in conditions of stress).

WO2008/115563 (University of Florida Research Foundation, 25 Sep. 2008) discloses a liquid food product composition suitable for—among a large number of medical applications—treating a large number of age-related disorders, such as sarcopenia, comprising at least one B-vitamin, vitamin C, vitamin E, creatine, leucine, taurine, a carbohydrate, GABA, ribose, (acetyl)carnitine, and a fat source, and optionally comprising a protein source (0.01-20 g), and vitamin D (0.01 to 1200 mg), the specific role of which is not disclosed.

EP 2 036 552 (Kao Corporation, 18 Mar. 2009) teaches compositions for treating muscle senescence, muscle dysfunction, muscular atrophy and related conditions containing catechin, optionally in combination with branched chain amino acids and/or taurine, as the active principle. Many different examples of useful formulations are disclosed. One of these examples concerns a standard multivitamin preparation including taurine and tea catechin. The standard multivitamin preparation includes vitamins according to the Japanese Recommended Dietary Allowance. No specific function of any one of the vitamins in the mixture is discussed or suggested in EP 2 036 552.

WO2009/143097 (Stokely-Van Camp Inc., 26 Nov. 2009) teaches a milk-based beverage comprising conjugated linoleic acid, milk proteins, carbohydrates, up to 1,000 IU of vitamin D and calcium for increasing muscle mass and decreasing body fat in sedentary individuals and athletes undergoing strength training.

EP 1 712 140 (Larena, 18 Oct. 2006) advocates a composition comprising i) natural protein rich in branched chain amino acids (BCAA), ii) an amino acid selected from arginine and glutamin, iii) ginsenosides, iv) zinc, v) selenium, vi) a vitamin selected from B1, B2, B3, B5, B6, B8, B9, B12, C, D and E, and vii) carotenoids. Most compositions disclosed contain a combination of whey and pea protein as the sources of the natural protein rich in BCAA and the arginine and/or glutamin.

Furthermore, a number of prior art documents, including JP 2008237070 and US 2010/0124587, address the problem of reducing the risks of fall related fractures in the elderly. Such compositions contain components aimed at increasing muscle mass or strength, thereby reducing the risk of falling, as well as a component aimed at increasing bone strength and/or density, thereby mitigating the consequences of falls. In these compositions vitamin D is used for increasing bone strength and/or density is.

None of the cited prior art documents disclose the combined use of an anabolic amino acid derivative stimulus and vitamin D, as active compounds working together, suitable for the prevention and/or treatment of a loss of any one of muscle mass, muscle strength, muscle function, and physical function, or any combination thereof, in an adult mammal, as well as to specific nutritional compositions suitable for stimulating muscle protein synthesis in an adult mammal.

The nutritional composition Resource® SeniorActiv (Nestle) commercially available since January 2010, is designed for the malnourished elderly, comprises a large number of components, among which milk proteins (10 g/100 ml, 7.5 g/100 kcal), vitamin D (250 IU/100 ml) and 150 kcal/100 ml of energy in a 200 ml serving, and has a dosage recommendation of 2 serving/day for use to help minimise muscle breakdown and support protein synthesis. It does not contain free amino acids derivatives, in particular free leucine.

SUMMARY DESCRIPTION OF THE INVENTION

Surprisingly, no research has been done on the relation between—on the one hand-protein deficiency (through inadequate protein intake) and the role of the activation signal generated by anabolic amino acids or anabolic amino acids derivative stimuli, and—on the other hand—vitamin D deficiency, both being associated with age-related loss of muscle mass in elderly. It was hypothesized that vitamin D, in particular high amounts of vitamin D, could play a crucial role in muscle sensitivity to the anabolic action of amino acids derivative stimuli. A nutritional product, rich in vitamin D, anabolic amino acid derivative stimuli and high-quality protein would then lead to an adequate stimulation of muscle protein synthesis and thus, of muscle mass gain, especially in sarcopenic persons, as it would simultaneously address the deficiencies in vitamin D and protein, as well as the resistance to anabolic action of amino acids on muscles.

Surprisingly, the inventors found that vitamin D, in particular high amounts of vitamin D as defined in the section "Vitamin D" below, enhances the stimulatory effect of anabolic amino derivative stimulus to stimulate muscle protein synthesis, and subsequent muscle mass gain. Without being bound by theory, it is hypothesized that the level of activation of the intracellular signalling pathways regulating muscle protein synthesis is higher when high amounts of vitamin D and an anabolic amino derivative stimulus are supplied sequentially or simultaneously to a person.

As a proof of concept that vitamin D enhances the stimulatory effect of anabolic amino acids on muscle protein synthesis, the activation of intracellular signalling pathway controlling protein synthesis in the presence or absence of vitamin D and leucine in an in vitro model was studied.

The combination is also useful for improving muscular-skeletal health in adult persons, for reducing the decline in muscular skeletal health in adult persons, for improving mobility in adult persons, for regaining and/or restoring muscular-skeletal functionality in adult persons after illness, surgery or injury; for reducing functional limitations in activities of daily living and hence, for improving activities of daily living, and for reducing the risk of falls and fall-related injuries.

DETAILED DESCRIPTION OF THE INVENTION

The invention is concerned with the use of an anabolic amino acid derivative stimulus acting in combination with vitamin D, as well as to a composition comprising said mutually active components, for the manufacture of a medicament or nutritional composition for the prevention and/or treatment of a loss of any one of muscle mass, muscle strength, muscle function, and physical function, or any combination thereof, in an a mammal, especially an adult mammal.

In the context of this application, the term "at least" also includes the starting point of the open range. For example, an amount of "at least 95 weight %" means any amount equal to 95 weight % or above.

In the context of this application, the term "about" means a deviation of 5% or less from the given value, such as 4%, 3%, 2%, 1%, or less than 1%. For example, an amount of "about 12 g" means any amount equal to 12 g±0.6 g, i.e. any amount in the range of 11.4 to 12.6 g. The reason for the use of the term "about" is to take into account the uncertainty associated with the analytical method to determine the specific component, or the variability of the manufacturing method when it concerns the manufacturing of a nutritional composition. According to a most preferred embodiment, about means 0%. Hence, an amount of "about 12 g" means "12 g".

In the context of this application, 1 IU of vitamin D is the biological equivalent of 0.025 μg. Hence, 1,000 IU is the biological equivalent of 25 μg.

With the term "proteinaceous matter" is meant a protein or any part derivable of a protein, such as but not limited to non-hydrolyzed protein, native protein, hydrolyzed protein, peptides, such as oligopeptides and dipeptides, and amino acids. Leucine is part of proteinaceous matter, citrulline, and creatine are not.

Anabolic Amino Acid Derivatives

The invention is related to the use of an anabolic amino acid derivative stimulus, which is defined as a chemical compound derived from or which is a precursor to an amino acid (hence, amino acid derivative) which promotes (hence, anabolic) muscle growth by increasing net protein synthesis (hence, stimulus).

Preferably, the anabolic amino acid derivative stimulus is one or more selected from the group of L-leucine, citrulline, and creatine. Most preferably, the anabolic amino acid derivative stimulus is an amino acid selected from the group of L-leucine and citrulline.

L-leucine (hereafter also called leucine, since the R-form of leucine is biologically not relevant in the context of this invention) is an essential amino acid, being part of a diverse number of proteins and, together with valine and isoleucine, belongs to the group of branched-chain amino acids. Leucine may be used as a free amino acid, or in a bound form, such as a dipeptide, an oligopeptide, a polypeptide or a protein. Common protein sources of leucine are dairy proteins such as whey, casein, micellar casein, caseinate, and glycomacroprotein (GMP), and vegetable proteins such as wheat, rice, pea, lupine and soy proteins. Said sources of protein may provide intact proteins, hydrolysates or mixtures thereof, hereafter further called proteinaceous matter. Leucine is known as a potent activator of muscle protein synthesis.

Citrulline is an α-amino acid. Its name is derived from citrullus, the Latin word for watermelon, as it is naturally present in watermelons. Citrulline, in the form of citrulline malate, is sold as a performance-enhancing athletic dietary supplement which was suggested to promote aerobic energy production (human study) [12] and to increase athletic performance and decreasing muscle soreness (human study) [13]. In the human body, citrulline is produced from ornithine and carbamoyl phosphate in one of the central reactions in the urea cycle. It is also produced from arginine in the body as a by-product of the reaction catalyzed by NOS family. Citrulline is also capable of promoting muscle protein synthesis and has been described in human and animal studies [see e.g. WO 2008/049984 by Université René Descartes-Paris, 2 May 2008]. Citrulline is commercially available and can be obtained, e.g. from Ajinomoto, Kyowa, and Biocodex.

Creatine (N-(amino-imino-methyl)-N-methyl-glycine; methylglycocyamine) is a nitrogenous organic acid that is produced in vertebrates, in particular the human body from L-arginine, glycine, and L-methionine and helps to supply energy to muscles. Creatine is commercially available and can be obtained, e.g. from Sigma Aldrich, Alfa Aesar, and Aminolabs.

Preferably, the anabolic amino acid derivative stimulus is provided in a daily dosage of 0.5 to 20 g, preferably 1 to 10 g. Preferably, such daily dosage is administered as a single serving.

In one embodiment, leucine is provided in a daily dosage of 1 to 10 g. When leucine is provided as proteinaceous matter, it should comprise at least about 11 weight % of leucine. It was found that about 11 weight % of total leucine based on the total amount of proteinaceous matter is a minimum amount present in the nutritional composition. Preferably, said proteinaceous matter comprises at least about 12 weight %, preferably at least about 12.5 weight %, more preferably at least about 13 weight % of leucine.

Preferably, total leucine comprises at least about 20 weight %, preferably at least about 22.5 weight %, preferably at least about 25 weight % of leucine in a free form, relative to the total amount of leucine. In the context of this application, with "free form" is meant a peptide comprising 1 to 5 amino acids, preferably 1 to 3 amino acids, more preferably 1 amino acid. Preferably, leucine is a free amino acid, either as a base, a salt or a chelate.

In one embodiment, citrulline is provided in a daily dosage of 0.5 to 10 g.

In one embodiment, creatine is provided in a daily dosage of 0.5 to 20 g.

In one embodiment, any combination of leucine, citrulline, and creatine is provided in a daily dosage of 0.5 to 20 g, preferably 1 to 10 g. Any combination is a combination selected from the group of leucine and citrulline; leucine and creatine; citrulline and creatine; and leucine, citrulline and creatine.

Vitamin D

Vitamin D is a group of fat-soluble secosteroids, the two major physiologically relevant forms of which are vitamin $D_2$ (ergocalciferol) and vitamin $D_3$ (cholecalciferol). These are known collectively as calciferol. Vitamin D without a subscript refers to all forms of vitamin D, either $D_1$, $D_2$, $D_3$, or $D_4$, in particular $D_2$ and $D_3$, or any mixture thereof.

When ingested, vitamin D is hydroxylated in the liver (endoplasmic reticulum) to 25-hydroxycholecalciferol (25 (OH)D), also known as calcidiol, by the enzyme 25-hydroxylase, produced by hepatocytes. Once made, the product is stored in the hepatocytes until it is needed and can be released into the plasma where it will be bound to an α-globulin. 25-hydroxycholecalciferol is then transported to the proximal tubules of the kidneys where it can be hydroxylated by one of two enzymes to different forms of vitamin D, one of which is active vitamin D (1,25(OH)D) and another which is inactive vitamin D (24,25(OH)D). The enzyme 1α-hydroxylase which is activated by parathyroid hormone (and additionally by low calcium or phosphate) forms the main biologically active vitamin D hormone with a C1 hydroxylation forming 1,25-dihydroxycholecalciferol (1,25 $(OH)_2D$, also known as calcitriol). A separate enzyme hydroxylates the C24 atom forming $24R,25(OH)_2D_3$ when 1α-hydroxylase is not active, this inactivates the molecule from any biological activity.

Vitamin D may be provided in an active (1,25($OH)_2D$) or unactive (Vit $D_3$ or $D_2$) form.

According to one embodiment, vitamin D is used in an amount of 800 IU or more per daily dosage, such as, for instance 1,000, 2,000, 3,000, 4,000, 5,000, 6,000, 7,000, 8,000, 9,000 or 10,000 IU, or any value in between any of two of said values or over, but not so high that it causes toxicity in the subject to whom it is administered.

According to one embodiment, vitamin D is used in an amount of 20 μg or more per daily dosage, such as, for instance 25, 50, 75, 100, 125, 150, 175, 200, 225 or 250 μg per daily dosage, or any value in between any of two of said values or over. Currently, the tolerable upper intake level (UL) in Europe and the US is set at 2,000 International Units (IU), equivalent to 50 μg per day. However, recent research, particularly from clinical trials, suggests that this should be raised to 10,000 IU (250 micrograms per day), as this dosage was not associated with any adverse or toxic effects.

Specifically preferred is a daily dose of vitamin D of more than 1,000 IU (25 μg).

Proteinaceous Matter

According to one embodiment, the anabolic amino acid derivative stimulus in combination with vitamin D is used for the manufacture of a medicament. In the context of this application, a medicament is an embodiment of the invention which does not, or does not substantially contain caloric components, such as carbohydrates, fat and proteinaceous matter, other than the components according to the invention. The medicament may be administered sequentially or simultaneously with said caloric components, in particular a protein source. Said caloric components may be provided separately, in the form of a meal, a food supplement, a drink, or in any other form.

According to an alternative embodiment, the anabolic amino acid derivative stimulus in combination with vitamin D is used for the manufacture of a nutritional composition. In the context of this application, a nutritional composition is an embodiment of the invention which contains, or substantially contains caloric components, such as carbohydrates, fat and proteinaceous matter, other than the components according to the invention.

According to one embodiment, the anabolic amino acid derivative stimulus in combination with vitamin D is used in combination with a source of proteinaceous matter to provide the necessary amino acids to prevent and/or treat a loss of muscle mass, a loss of muscle function, or both, in an adult mammal. The source of proteinaceous matter may be provided separately, in the form of a meal, a food supplement, a drink, or in any other form or may be combined in a single nutritional composition.

Preferably, the proteinaceous matter originates from high quality protein, such as dairy proteins, such as whey or casein. The amino acids are essentially L-amino acids as only L-amino acids are metabolically relevant in the context of this invention.

Preferably, the nutritional composition according to the invention comprises at least about 12 g of proteinaceous matter per 100 kcal.

Preferably, the composition comprises at least about 12.5 g, at least about 13 g, at least about 13.5 g, and most preferably about 14 g of proteinaceous matter per 100 kcal.

According to another embodiment, the nutritional composition according to the invention comprises at least about 45 en % of proteinaceous matter per 100 kcal. Preferably, the composition comprises at least about 48 en %, at least about 50 en %, at least about 52 en %, at least about 54 en %, and most preferably at least about 56 en % of proteinaceous matter per 100 kcal.

According to a preferred embodiment, the proteinaceous matter according to the invention comprises at least about 80 weight % of whey protein, preferably at least about 85 weight % of whey protein, preferably at least about 90 weight %, and most preferably about 95 weight % of whey protein.

Whey protein is considered a "fast" protein referring to the rate of appearance in the circulation of the amino acids following whey ingestion. The whey protein may be an intact whey protein, a hydrolysed whey protein, a microparticular whey protein, a nanoparticular whey protein, a micellar whey protein, and the like. Preferably, the whey protein is an intact whey protein, i.e. a whey protein in its intact form, such as present in fresh milk.

As a source of whey protein to be used in the present invention, any commercially available whey protein source may be used, i.e. whey obtained by any process for the preparation of whey known in the art, as well as whey protein fractions prepared thereof, or the proteins that constitute the bulk of the whey proteins being ß-lactoglobulin, α-lactalbumin and serum albumin, such as liquid whey, or whey in powder form, such as whey protein isolate (WPI) or whey protein concentrate (WPC). Whey protein concentrate is rich in whey proteins, but also contains other components such as fat, lactose and glycomacroprotein (GMP), a casein-related non-globular protein. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultra-filtration or ion exchange chromatography. It is generally understood that a whey protein isolate refers to a mixture in which at least 90 weight % of the solids are whey proteins. A whey protein concentrate is understood as having a percentage of whey proteins between the initial amount in the by-product (about 12 weight %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used as a source of whey proteins.

Furthermore, whey proteins may originate from all kinds of mammalian animal species, such as, for instance cows, sheep, goats, horses, buffalo's, and camels. Preferably, the whey protein is of bovine origin.

Preferably, the whey protein source is available as a powder, preferably the whey protein source is a WPC or WPI.

According to another embodiment, the proteinaceous matter according to the invention comprises at least about 45 weight % of essential amino acids (EAA), preferably at least about 47 weight %, and more preferably at least about 50 weight % of EAA. Essential amino acids are amino acids selected from the group of isoleucine (Ile), leucine (Leu), lysine (Lys), methionine (Met), phenylalanine (Phe), threonine (Thr), tryptophan (Trp), and valine (Val). Since native whey protein and casein protein comprise (depending on the source) maximum about 45 and 41 weight % of EAA, respectively, it may be necessary to add EAA's to the nutritional composition, such as in the form of amino acids or peptides, to arrive at the preferred amount of at least 45 weight %.

According to another embodiment, the proteinaceous matter according to the invention comprises total leucine, total valine and total isoleucine in a total leucine:valine:isoleucine ratio of about 1.7-3:1:1. Alternatively, the weight ratio of leucine: (valine+isoleucine) is about 0.9 or higher, preferably 1.0 or higher. Suitable valine and isoleucine levels may be provided by the whey protein, or may be provided by added amino acids, either in free form as bases or salts, or as peptides.

Surprisingly, the inventors found that essential amino acids, in particular leucine, showed an improved bioavailability of amino acids to stimulate muscle protein synthesis and subsequent muscle mass when essential amino acids were administered using a, low-caloric ((being defined as not exceeding 100 kcal/100 ml) nutritional composition. Without being bound by theory, it is hypothesized that amino acids reach the circulation faster and reach higher blood levels when dietary protein is given in a low-caloric composition compared to a high-caloric composition, preferably using whey, although the effect is the same but smaller for casein. This so called "low-energy effect" could beneficially be used for treatment of persons suffering from any disease, the prevention and treatment of which is related to the synthesis of muscle protein, in particular, sarcopenia, a disease which involves muscle decline with insufficient (net) muscle protein synthesis and muscle decline, associated with aging.

Fat and Carbohydrates

According to a preferred embodiment, the nutritional composition according to the invention comprises at least one of a source of fat and a source of carbohydrates. The presence of one or both of these components effectively prohibits the excessive use of the protein as an energy source instead of for stimulating muscle protein synthesis.

The total amount of energy supplied by the fat and/or carbohydrates (digestible and indigestible) should match the total energy supplied by the proteinaceous matter. Therefore, the total amount fat and/or carbohydrates should be at most about 55 en %, preferably at most about 52 en %, preferably at most about 48 en %, preferably at most about 44 en %.

The amount of energy supplied by respectively the fat and/or the carbohydrates may vary within wide limits, as long as both components are present. More specifically, the amount of fat may vary between 10 and 35 en %, preferably between 15 and 30 en %. More specifically, the amount of carbohydrate may vary between 10 and 35 en %, preferably between 15 and 30 en %. Hence, the relative amounts of the sum of fat and carbohydrate range between 30 and 60 en %.

In a preferred embodiment, the nutritional composition according to the invention comprises a source of fat and a source of carbohydrates, preferably in an amount of about 2 g of fat and about 6.4 g of digestible carbohydrates per 100 kcal.

With regard to the type of fat, a wide choice is possible, as long as the fat is of food quality.

The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. In one embodiment, the present composition comprises rapeseed oil, corn oil and/or sunflower oil. The fat may include a source of medium chain fatty acids, such as medium chain triglycerides (MCT, mainly 8 to 10 carbon atoms long), a source of long chain fatty acids, such as long chain triglycerides (LCT) and phospholipid-bound fatty acids such as phospholipid-bound EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body.

With regard to the type of carbohydrates, a wide choice is possible, as long as the carbohydrates are of food quality. The digestible carbohydrates positively influence the energy level of a subject, and add to the advantageous effect of the nutritional composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and poly-saccharides.

Dietary Fibers

The liquid enteral nutritional composition according to the invention may optionally be fortified with dietary fibres (or prebiotics fibres) such as non-digestible carbohydrates such as galacto-oligosaccharides, fructo-oligosaccharides, inulin, and pectin (hydrolysed pectin, low-viscosity pectin (a pectin degradation product with a DP of 2-250), or other pectin degradation products). In an embodiment of the present invention, the composition according to the invention comprises 0.5 g/100 kcal to 6 g/100 kcal of non-digestible carbohydrates. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylo-oligosaccharides (XOS), soy oligosaccharides, and the like. Optionally, also higher molecular weight compounds such as inulin, soy polysaccharides, acacia polysaccharides (acacia fibre or arabic gum), cellulose, resistant starch and the like may be incorporated in the composition according to the invention. The amount of insoluble fibre such as cellulose is preferably lower than 20 weight % of the dietary fibre fraction of the composition according to the invention, and/or below 0.6 g/100 kcal. The amount of thickening polysaccharides such as carrageenans, xanthans, pectins, galactomannans and other high molecular weight (DP>50) indigestible polysaccharides is preferably low, i.e. less than 20% of the weight of the fibre fraction, or less than 1 g/100 kcal. Instead, hydrolysed polysaccharides such as hydrolysed pectins and galactomannans can advantageously be included.

A preferred fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructo-oligosaccharides or galacto-oligosaccharides (GOS), which may also contain a small amount of higher saccharides (e.g. with a DP of 11 to 20). Such oligosaccharides preferably comprise 50 weight % to 90 weight % of the fibre fraction, or 0.5 g/100 kcal to 3 g/100 kcal of the composition according to the invention. Other suitable fibre components include saccharides that have only partial digestibility.

In a particular embodiment, the composition according to the invention comprises one or more of fructo-oligosaccharides, inulin, acacia polysaccharides, soy polysaccharides, cellulose and resistant starch.

In another embodiment of the present invention, the composition according to the invention may comprise a mixture of neutral and acid oligosaccharides as disclosed in WO 2005/039597 (N.V. Nutricia), which is incorporated herein by reference in its entirety.

More in particular, the acid oligosaccharide has a degree of polymerization (DP) between 1 and 5000, preferably between 1 and 1,000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1,000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, α-D-galactopyranose, ribose, glucose, xylose and derivatives thereof, calculated on the total number of monose units contained therein. Suitable neutral oligosaccharides are preferably fermented by the gut flora. Preferably, the oligosaccharide is selected from the group consisting of: cellobiose (4-O-β-D-glucopyranosyl-D-glucose), cellodextrins ((4-O-β-D-glucopyranosyl)$_n$-D-glucose), β-cyclodextrins (cyclic molecules of α-1-4-linked D-glucose; α-cyclodextrin-hexamer, β-cyclodextrin-heptamer and γ-cyclodextrin-octamer), indigestible dextrin, gentiooligosac-charides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-gluco-pyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B—D-fructofuranoside), D-agatose, D-lyxohexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosac-charides (β-D-galactopyranosyl-(1-6)-[β-D-glucopyranosyl]$_n$-(1-4)  α-D glucose), lactulose (4-O-β-D-galactopyranosyl-D-fructose), 4'-galatosyllactose  (O-D-galactopyranosyl-(1-4)-O-β-D-glucopyranosyl-(1-4)-D-glucopyranose), synthetic galactooligosaccharide (neogalacto-biose, isogalactobiose, galsucrose, isolactose I, II and III), fructans—Levan-type (β-D-(2→6)-fructofuranosyl)$_n$ α-D-glucopyranoside), fructans—Inulin-type (β-D-((2→1)-fructo-furanosyl)$_n$ α-D-glucopyranoside), 1 f-β-fructofuranosylnystose (β-D-((2→1)-fructofurano-syl)$_n$ B—D-fructofuranoside), xylooligosaccharides (B—D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galacto-oligosaccharides (including transgalactooligosaccharides), xylooligosaccharides, arabino-oligosaccharides, glucooligosaccharides, mannooligosaccharides, fucooligosaccharides and mixtures thereof. Most preferably, the neutral oligosaccharide is selected from the group consisting of fructooligosachararides, galactooligosaccharides and transgalactooligo-saccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin (such as hydrolysed pectin (an acid oligosaccharide (AOS)) and low-viscosity pectin), alginate, and mixtures thereof; and a neutral oligosaccharide, selected from the group of fructans, fructooligosaccharides, indigestible dextrins, galactooligosaccharides including transgalactooligosaccharides, xylooligosaccharides, arabinooligosaccharides, glucooligo-saccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect. Preferably, the composition according to the invention comprises:
- an acid oligosaccharides as defined above (preferably low-viscosity pectin);
- a galactose-based neutral oligosaccharide (of which more than 50% of the monose units are galactose units), preferably selected from the group consisting of galactooligosaccharide and transgalactooligosaccharide; and
- a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

Preferably, the nutritional composition further comprises one or more dietary fibres selected from the group of short chain GOS, long chain FOS, inulin and low-viscosity pectin.

Particular Embodiments of the Nutritional Composition

In a particular preferred embodiment, the nutritional composition comprises per 100 kcal:
(i) about 14 g of proteinaceous matter which comprises about 95 weight % of whey protein, relative to the total proteinaceous matter, and which comprises at least about 14 weight % of leucine, relative to the total proteinaceous matter, of which at least about 26 weight % is in a free form, relative to the total leucine, (ii) about 2 g of fat and about 6.4 g of digestible carbohydrates, and (iii) about 532 IU (13.3 µg) of vitamin D, for the manufacture of a medicament for the prevention or treatment of a disease which involves muscle decline in an adult mammal, wherein the nutritional composition is administered as 1 to 2 servings daily, each serving comprising about 150 kcal.

In another particular preferred embodiment, the nutritional composition comprises per 100 kcal:

(i) about 12 g of proteinaceous matter which comprises about 90 weight % of whey protein, relative to the total proteinaceous matter, and which comprises at least about 16 weight % of leucine, relative to the total proteinaceous matter, of which at least about 45 weight % is in a free form, relative to the total leucine, (ii) about 1.5 g of fat, and about 8.3 g of digestible carbohydrates, and (iii) about 640 IU (16 µg) of vitamin D, for the manufacture of a medicament for the prevention or treatment of a disease which involves muscle decline in an adult mammal, wherein the nutritional composition is administered as 1 to 2 servings daily, each serving comprising about 125 kcal.

Micronutrients

Elderly are at risk for micronutrient deficiencies, which is partly due to the fact that their energy intake is often reduced while many micronutrients recommendations increase [14]. As a result, 25-60% of the elderly does not meet the recommendations for micronutrient intake, and deficiencies of vitamins such as A, C, D, E, B6, folic acid, B12, calcium, magnesium, and zinc are commonly reported [15-17]. Moreover, micronutrients are associated with frailty. Low intake of vitamin D, E, C and folate were associated with frailty [18], and low serum levels of carotenoids, vitamin E, vitamin D, selenium and zinc were observed in frail versus non-frail elderly [19].

Of the micronutrients, selenium, zinc, carotenoids, vitamin C and vitamin E all have antioxidant properties. Related to the published observation on the reversion by antioxidant supplementation of the decreased ability of leucine to stimulate muscle protein synthesis in elderly rats [20], a mixture of antioxidants is included in the nutritional composition.

The B-vitamins folic acid, vitamin B6 and vitamin B12 are involved in the metabolic pathway of homocysteine, a known risk factor for common diseases in elderly [21], and are commonly deficient in elderly [17]. Because of the beneficial effect of folic acid, vitamin B6 and vitamin B12 on lowering blood homocysteine levels, these vitamins are present in the nutritional composition.

Hence, the nutritional composition according to the invention may optionally further comprise one or more micronutrients, defined as minerals, trace elements and vitamins, selected from the group of sodium, potassium, chloride, calcium, phosphorous, magnesium, carotenoids, vitamin A, vitamin E, vitamin K, vitamin B1, vitamin B2, vitamin B3, vitamin B5, vitamin B6, folic acid, vitamin B12, biotin, vitamin C, zinc, iron, copper, manganese, molybdenum, selenium, chromium, fluoride and iodide. Preferably, the micronutrients are selected from the group of carotenoids, vitamin A, vitamin B6, vitamin B12, vitamin C, vitamin E, folic acid, calcium, phosphorus, magnesium, zinc and selenium. Preferably, the nutritional composition according to the invention may further comprise carotenoids, vitamin B6, vitamin C, vitamin E, folic acid, vitamin B12, selenium and zinc. Preferably, the nutritional composition according to the invention may further comprise per 100 kcal 10 to 500 mg of carotenoids, 8 to 750 µg of vitamin B6, 2.25 to 25 mg of vitamin C, 0.5 to 10 mg of vitamin E, 10 to 150 µg of folic acid, 0.07 to 5 µg of vitamin B12, 2.5 to 20 µg of selenium and 0.5 to 2.0 mg of zinc.

Medical Use

The nutritional composition according to the invention can advantageously be used for the manufacture of a medicament for the prevention or treatment of a disease or condition involving muscle decline in an a mammal, especially an adult mammal. Alternatively, the nutritional composition according to invention can advantageously be used for the manufacture of a medicament for the prevention or treatment of a disease or condition selected from the group of sarcopenia, muscle loss, insufficient muscle protein synthesis, muscle degradation, muscle proteolysis, muscle atrophy, muscle dystrophy, muscle catabolism, muscle wasting, loss of muscle strength, loss of muscle mass, loss of muscle function, loss of physical capacity, loss of physical performance, impaired mobility, frailty, surgery, disability, risk of falling and risk of fall-related fractures.

Preferably, said adult mammal is an elderly human. In this respect, it is submitted that in the context of this application, an elderly human is a person of the age of 50 years or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

The nutritional composition according to the invention can advantageously be used for the prevention or treatment of muscle decline, in particular loss of muscle mass, during or following body weight maintenance, during or following energy restriction, during or following bed rest or during recovery following physical trauma. In a particularly preferred embodiment the compositions of the invention are used in the treatment of a subject, e.g. a subject suffering from overweight or obesity, said subject following a weight loss program, an energy restriction program and/or an exercise program. Said subject may be a child, an adolescent, an adult or an elderly subject. In an embodiment said subject is a child, an adolescent or an adult.

Dosage

The nutritional composition is administered as 1 to 2 servings daily, each serving comprising between 80 and 200 kcal, preferably about 125 kcal, preferably about 150 kcal. Preferably, the nutritional composition is administered as one serving daily. Using a nutritional composition in a liquid or spoonable form, the serving may comprise 30 to 250 ml of nutritional composition according to the invention, most preferably 200 ml per serving. Using a nutritional composition in a solid form, such as a powder, the serving may comprise 20 to 100 g of nutritional composition according to the invention, most preferably 30 to 70 g per serving, most preferably about 40 g per serving.

Nutritional Compositions

The present invention relates also to a composition comprising at least an anabolic amino acid derivative stimulus combination with vitamin D, preferably in an amount of 800 IU or more per daily dosage.

The present invention relates also to specific low-caloric (being defined as not exceeding 100 kcal/100 ml) high-protein nutritional compositions suitable for stimulating muscle protein synthesis, either in liquid, in spoonable or in solid form.

According to one embodiment, the invention concerns a liquid or spoonable nutritional composition comprising:
(i) not more than about 100 kcal of energy per 100 ml of liquid or spoonable nutritional composition,
(ii) at least about 10 g proteinaceous matter per 100 ml of liquid or spoonable nutritional composition, comprising at least about 80 weight % of whey protein, relative to the total proteinaceous matter,
(iii) at least about 1 g leucine per 100 ml of liquid or spoonable nutritional composition, of which at least about 20 weight % is in a free form, relative to the total amount of leucine,
(iv) at least about 400 IU of vitamin D per 100 ml of liquid or spoonable nutritional composition, and
(v) a source of fat and a source of digestible carbohydrates.

According to another embodiment, the invention concerns a liquid nutritional composition comprising:
(i) about 100 kcal of energy per 100 ml of liquid nutritional composition,
(ii) about 12 g proteinaceous matter per 100 ml of liquid nutritional composition comprising about 10.8 g whey protein per 100 ml of liquid nutritional composition,
(iii) about 2 g leucine per 100 ml of liquid nutritional composition of which about 1 g per 100 ml of liquid nutritional composition is in a free form,
(iv) at least about 640 IU vitamin D per 100 ml of liquid nutritional composition,
(v) about 2 g fat per 100 ml of liquid nutritional composition, comprising a total of 400 mg of DHA and EPA per 100 ml of liquid nutritional composition and about 8.3 g digestible carbohydrates per 100 ml of liquid nutritional composition,
(vi) optionally, a source of dietary fibre, and,
(vii) optionally, additional micronutrient(s).

According to another embodiment, the invention concerns a liquid nutritional composition comprising:
(i) about 100 kcal of energy per 100 ml of liquid nutritional composition,
(ii) about 12 g proteinaceous matter per 100 ml of liquid nutritional composition comprising about 10.8 g whey protein per 100 ml of liquid nutritional composition,
(iii) about 2 g leucine per 100 ml of liquid nutritional composition of which about 1 g per 100 ml of liquid nutritional composition is in a free form, and about 1 g citrulline per 100 ml of liquid nutritional composition
(iv) at least about 640 IU vitamin D per 100 ml of liquid nutritional composition,
(v) about 2 g fat per 100 ml of liquid nutritional composition, comprising a total of 400 mg of DHA and EPA per 100 ml of liquid nutritional composition and about 8.3 g digestible carbohydrates per 100 ml of liquid nutritional composition,
(vi) optionally, a source of dietary fibre, and,
(vii) optionally, additional micronutrient(s)

Preferably, the liquid or spoonable nutritional composition according to the invention comprises less than 90 kcal, preferably less than 80 kcal of energy per 100 ml of liquid nutritional composition.

According to another embodiment, the invention concerns a liquid nutritional composition comprising:
(i) about 75 kcal of energy per 100 ml of liquid nutritional composition,
(ii) about 10.5 g proteinaceous matter per 100 ml of liquid nutritional composition comprising about 10 g whey protein per 100 ml of liquid nutritional composition,
(iii) about 1.5 g leucine per 100 ml of liquid nutritional composition of which about 0.4 g per 100 ml of liquid nutritional composition is in a free form,
(iv) at least about 400 IU vitamin D per 100 ml of liquid nutritional composition,
(v) about 1.5 g fat per 100 ml of liquid nutritional composition and about 4.8 g digestible carbohydrates per 100 ml of liquid nutritional composition,
(vi) optionally, a source of dietary fibre, and,
(vii) optionally, additional micronutrient(s).

According to another embodiment, the invention concerns a liquid nutritional composition comprising:
(i) about 75 kcal of energy per 100 ml of liquid nutritional composition,
(ii) about 10.5 g proteinaceous matter per 100 ml of liquid nutritional composition comprising about 10 g whey protein per 100 ml of liquid nutritional composition,
(iii) about 1 g leucine per 100 ml of liquid nutritional composition, about 0.5 g citrulline per 100 ml of liquid nutritional composition, and about 2.5 g creatine per 100 ml of liquid nutritional composition,
(iv) at least about 400 IU of vitamin D per 100 ml of liquid nutritional composition, and
(v) about 1.5 g fat per 100 ml of liquid nutritional composition and about 4.8 g digestible carbohydrates per 100 ml of liquid nutritional composition,
(vi) optionally, a source of dietary fibre, and
(vii) optionally, additional micronutrient(s).

According to another embodiment, the invention concerns a liquid nutritional composition comprising:
(i) about 75 kcal of energy per 100 ml of liquid nutritional composition,
(ii) about 10.5 g proteinaceous matter per 100 ml of liquid nutritional composition comprising about 10 g whey protein per 100 ml of liquid nutritional composition,
(iii) about 1 g leucine per 100 ml of liquid nutritional composition and about 1 g citrulline per 100 ml of liquid nutritional composition,
(iv) at least about 400 IU vitamin D per 100 ml of liquid nutritional composition,
(v) about 1.5 g fat per 100 ml of liquid nutritional composition and about 4.8 g digestible carbohydrates per 100 ml of liquid nutritional composition,
(vi) optionally, a source of dietary fibre, and
(vii) optionally, additional micronutrient(s).

According to another embodiment, the invention concerns a liquid nutritional composition comprising:
(i) about 75 kcal of energy per 100 ml of liquid nutritional composition,
(ii) about 10.5 g proteinaceous matter per 100 ml of liquid nutritional composition comprising about 10 g whey protein per 100 ml of liquid nutritional composition,
(iii) about 1 g leucine per 100 ml of liquid nutritional composition and about 2.5 g creatine per 100 ml of liquid nutritional composition, (iv) at least about 400 IU vitamin D per 100 ml of liquid nutritional composition,
(v) about 1.5 g fat per 100 ml of liquid nutritional composition and about 4.8 g digestible carbohydrates per 100 ml of liquid nutritional composition,
(vi) optionally, a source of dietary fibre, and
(vii) optionally, additional micronutrient(s).

According to another embodiment, the invention concerns a spoonable nutritional composition comprising:
(i) about 75 kcal of energy per 100 ml of spoonable nutritional composition,
(ii) about 10.5 g proteinaceous matter per 100 ml of spoonable nutritional composition comprising about 10 g whey protein per 100 ml of spoonable nutritional composition,
(iii) about 1.5 g leucine per 100 ml of spoonable nutritional composition of which about 0.4 g per 100 ml of spoonable nutritional composition is in a free form,
(iv) at least about 400 IU vitamin D per 100 ml of spoonable nutritional composition,
(v) about 1.5 g fat per 100 ml of spoonable nutritional composition and about 4.8 g digestible carbohydrates per 100 ml of spoonable nutritional composition,
(vi) optionally, a source of dietary fibre, and,
(vii) optionally, additional micronutrient(s).

When a source of dietary fibre is added to the above composition, it is preferable to add a total amount of about 0.83 g of dietary fibre comprising 0.63 g of GOS, 0.07 g of FOS/inulin and 0.14 g of low-viscosity pectin.

When additional micronutrient(s) are added to the above composition, one or more micronutrients are preferably selected from the group of sodium, potassium, chloride, calcium, phosphorous, magnesium, carotenoids, vitamin A, vitamin E, vitamin K, vitamin B1, vitamin B2, vitamin B3, vitamin B5, vitamin B6, folic acid, vitamin B12, biotin, vitamin C, zinc, iron, copper, manganese, molybdenum, selenium, chromium, fluoride and iodide.

Said high amounts of whey protein can be achieved using inventive processes such as disclosed in WO 2009/113858, the contents of which are incorporated herein by reference.

According to one embodiment, the nutritional composition is packaged as a 30 to 300 ml serving, more preferably as a 200 ml serving.

According to one embodiment, the invention concerns a solid nutritional composition comprising:
(i) less than about 500 kcal of energy per 100 g of dry weight,
(ii) at least about 49 g proteinaceous matter per 100 g of dry weight of comprising at least about 80 weight % of whey protein, relative to the total proteinaceous matter,
(iii) at least about 5 g leucine per 100 g of dry weight of which at least about 20 weight % is in a free form, relative to the total leucine,
(iv) at least about 50 µg of vitamin D per 100 g of dry weight, and
(v) a source of fat and a source of digestible carbohydrates.

The solid nutritional composition according to the invention comprises per 100 g, less than 445 kcal, preferably less than 395 kcal of energy.

According to one embodiment, the invention concerns a solid nutritional composition comprising:
(i) about 375 kcal of energy per 100 g of dry weight,
(ii) about 53 g proteinaceous matter per 100 g of dry weight which comprises about 50 g whey protein per 100 g of dry weight,
(iii) about 7.5 g leucine per 100 g of dry weight of which about 2 g per 100 g is in a free form,
(iv) at least about 50 µg of vitamin D per 100 g of dry weight,
(v) about 7.5 g fat per 100 g of dry weight and about 24 g digestible carbohydrates per 100 g of dry weight,
(vi) optionally, a source of dietary fibre, and
(vii) optionally, additional micronutrient(s).

According to one embodiment, the invention concerns a solid nutritional composition comprising:
(i) about 375 kcal of energy per 100 g of dry weight,
(ii) about 51 g proteinaceous matter per 100 g of dry weight which comprises about 50 g whey protein per 100 g of dry weight,
(iii) about 5.5 g leucine per 100 g of dry weight, about 2.5 g citrulline per 100 g of dry weight, and about 12.5 g creatine per 100 g of dry weight,
(iv) at least about 50 µg of vitamin D per 100 g of dry weight,
(v) about 7.5 g fat per 100 g of dry weight and about 24 g digestible carbohydrates per 100 g of dry weight,
(vi) optionally, a source of dietary fibre, and
(vii) optionally, additional micronutrient(s).

According to one embodiment, the invention concerns a solid nutritional composition comprising:
(i) about 375 kcal of energy per 100 g of dry weight,
(ii) about 51 g proteinaceous matter per 100 g of dry weight which comprises about 50 g whey protein per 100 g of dry weight,
(iii) about 5.5 g leucine per 100 g of dry weight, and about 2.5 g citrulline per 100 g of dry weight,
(iv) at least about 50 µg of vitamin D per 100 g of dry weight,
(v) about 7.5 g fat per 100 g of dry weight and about 24 g digestible carbohydrates per 100 g of dry weight,
(vi) optionally, a source of dietary fibre, and
(vii) optionally, additional micronutrient(s).

According to one embodiment, the invention concerns a solid nutritional composition comprising:
(i) about 375 kcal of energy per 100 g of dry weight,
(ii) about 51 g proteinaceous matter per 100 g of dry weight which comprises about 50 g whey protein per 100 g of dry weight,
(iii) about 5.5 g leucine per 100 g of dry weight and about 5 g citrulline per 100 g of dry weight,
(iv) at least about 50 µg of vitamin D per 100 g of dry weight,
(v) about 7.5 g fat per 100 g of dry weight and about 24 g digestible carbohydrates per 100 g of dry weight,
(vi) optionally, a source of dietary fibre, and
(vii) optionally, additional micronutrient(s).

According to one embodiment, the invention concerns a solid nutritional composition comprising:
(i) about 375 kcal of energy per 100 g of dry weight,
(ii) about 51 g proteinaceous matter per 100 g of dry weight which comprises about 50 g whey protein per 100 g of dry weight,
(iii) about 5.5 g leucine per 100 g of dry weight and about 12.5 g creatine per 100 g of dry weight,
(iv) at least about 50 µg of vitamin D per 100 g of dry weight,
(v) about 7.5 g fat per 100 g of dry weight and about 24 g digestible carbohydrates per 100 g of dry weight,
(vi) optionally, a source of dietary fibre, and
(vii) optionally, additional micronutrient(s).

When a source of dietary fibre is added to the above compositions, it is preferable to add a total amount of 4.13 g of dietary fibre comprising about 3.1 g of GOS, 0.34 g of FOS/inulin and 0.19 g of low-viscosity pectin.

When additional micronutrient(s) are added to the above compositions, one or more micronutrients are preferably selected from the group of sodium, potassium, chloride, calcium, phosphorous, magnesium, carotenoids, vitamin A, vitamin E, vitamin K, vitamin B1, vitamin B2, vitamin B3, vitamin B5, vitamin B6, folic acid, vitamin B12, biotin, vitamin C, zinc, iron, copper, manganese, molybdenum, selenium, chromium, fluoride and iodide.

Preferably, the solid nutritional composition according to the invention is formed as a powder, capable of being dissolved in an aqueous solution.

Preferably, the solid nutritional composition according to the invention is presented as a serving of about 20 to 70 g, more preferably of about 40 g.

The powder may be presented as a sachet, a cup, and the like, having the size of about the size of a serving, or it may be presented in a container, comprising several servings, such as 10 to 25 servings, optionally accompanied by a metering device such as a spoon.

With regard to the liquid, spoonable, and solid nutritional composition according to the invention, one or more of the following specifications apply:
- the amount of fat may vary between 10 and 35 en %, preferably between 15 and 30 en %;
- the amount of carbohydrate may vary between 10 and 35 en %, preferably between 15 and 30 en %;
- the relative amounts of the sum of fat and carbohydrate range between 30 and 60 en %;
- the proteinaceous matter comprises at least about 85 weight % of whey protein, preferably at least about 90 weight %, and more preferably about 95 weight % of whey protein.
- the proteinaceous matter comprises at least 45 weight %, preferably at least 47 weight %, and more preferably at least about 50 weight % of essential amino acids (EAA).
- the proteinaceous matter comprises at least about 12 weight %, preferably at least about 12.5 weight %, more preferably at least about 13 weight % of leucine.
- the proteinaceous matter comprises at least about 22.5 weight %, preferably at least about 25 weight % of leucine in a free form, relative to the total amount of leucine.
- the proteinaceous matter comprises total leucine, total valine and total isoleucine in a total leucine:valine:isoleucine ratio of about 1.7-3:1:1.
- the nutritional composition further comprises one or more dietary fibres selected from the group of short chain GOS, long chain FOS, inulin and low-viscosity pectin.
- the nutritional composition further comprises one or micronutritients selected from the group of sodium, potassium, chloride, calcium, phosphorous, magnesium, carotenoids, vitamin A, vitamin E, vitamin K, vitamin B1, vitamin B2, vitamin B3, vitamin B5, vitamin B6, folic acid, vitamin B12, biotin, vitamin C, zinc, iron, copper, manganese, molybdenum, selenium, chromium, fluoride and iodide.

The compositions according to the invention may be prepared by the methods as disclosed in WO 2009/113858, which is incorporated herein by reference in its entirety. Powders can be made by methods commonly known in the art by the skilled person, such as spray drying the liquid composition.

Experiment Summary

An experimental in vitro study is performed to evaluate the synergistic or additional action of leucine and vitamin D on intracellular pathways regulating protein synthesis in muscle cells.

C2C12 mouse myoblasts are obtained from the American Type Culture Source Collection (no. CRL-1772). Myoblasts are cultured at 37° C. in an atmosphere of 5% CO2 in grown medium consisting of Dulbecco's modified Eagle's medium (DMEM) supplemented with 10% foetal calf serum and antibiotics. Myotube C2C12 differentiation is induced by withdrawing foetal calf serum from confluent cells and adding 10 µg/ml insulin, 5 µg/ml transferrin and 2% horse serum.

Confluent C2C12 myotubes are treated with vehicles alone or with different doses of 1,25(OH)2 D3. Subsequently, the cells are deprived of horse serum by incubation in a serum-free medium for the two remaining hours. During this deprivation period, different amounts of leucine and insulin are added to the medium before harvesting cells.

Medium with or without leucine supplementation are used to assess the synergistic or additional action of leucine and vitamin D on intracellular pathways regulating protein synthesis (Akt, mTOR) and/or on direct measure of protein synthesis.

Figure 1:
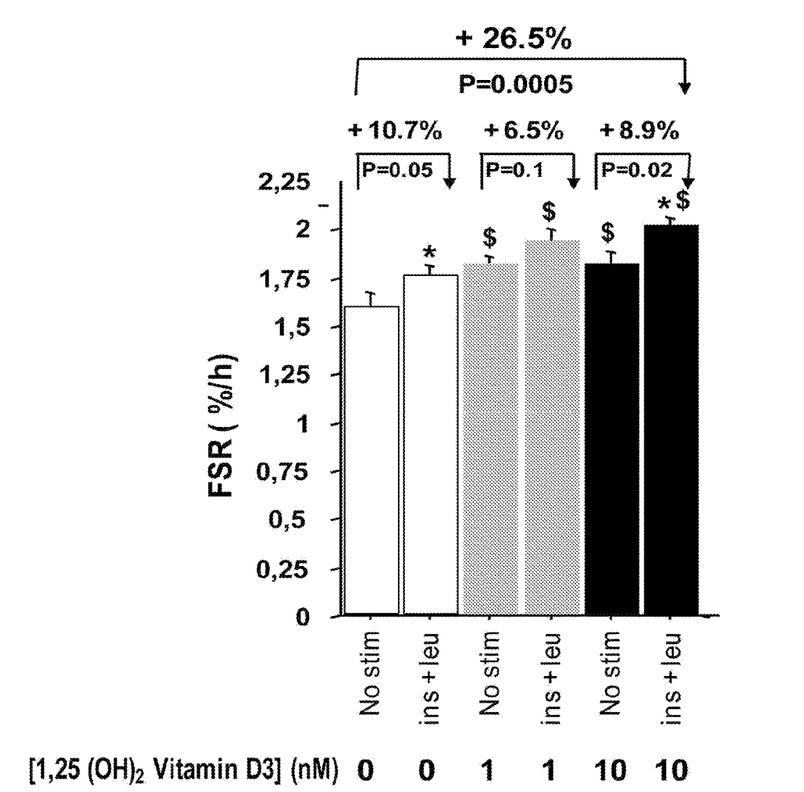
FIG. 1: Protein synthesis rate (FSR) in C2C12 myotubes after 72 h pretreatments with 0, 1 or 10 nm of 1,25(OH)2 Vitamin $D_3$. N=5 for every condition. *: $p<0.05$ vs no stimulation for the same vitamin D concentration. $: $p<0.05$ vs 0 nM of vitamin D for the same stimulation.

Protein synthesis rate (FSR) in C2C12 myotubes after 72 h pretreatments with 0, 1 or 10 nm of 1,25(OH)2 Vitamin $D_3$ is depicted in FIG. 1. The change (%) in protein synthesis rate vs no pretreatment with vitamin $D_3$ is summarized in table 1.

As shown in FIG. 1, vitamin $D_3$ (dose 1 or 10 nM) can stimulate muscle protein synthesis independently of leucine presence (no stimulation). More importantly, when myotubes are treated with both leucine and vitamin $D_3$, the increase in muscle protein synthesis rate (+26.4%) is higher than the sum of the response obtained when the cells are treated only with vitamin $D_3$ (+14.3%) or with leucine alone (+10.7%).

Taken together, these results clearly support the synergic action of leucine and vitamin $D_3$ to promote muscle protein synthesis.

TABLE 1

|  | [Vitamin D] = 1 nM | | [Vitamin D] = 10 nM | |
|---|---|---|---|---|
|  | No stim | Ins + leu | No stim | Ins + leu |
| [Vit D] = 0  No stim | 14.0* |  | 14.3* |  |
| Ins + leu |  | 9.8* |  | 14.3* |

REFERENCES

1. Rolland, Y., et al., Sarcopenia: its assessment, etiology, pathogenesis, consequences and future perspectives. J Nutr Health Aging, 2008. 12(7): p. 433-50.

2. Dardevet, D., et al., *Stimulation of in vitro rat muscle protein synthesis by leucine decreases with age.* J Nutr, 2000. 130(11): p. 2630-5.
3. Katsanos, C. S., et al., *Aging is associated with diminished accretion of muscle proteins after the ingestion of a small bolus of essential amino acids.* Am J Clin Nutr, 2005. 82(5): p. 1065-73.
4. Cuthbertson, D., et al., *Anabolic signaling deficits underlie amino acid resistance of wasting, aging muscle.* Faseb J, 2005. 19(3): p. 422-4.
5. Guillet, C., et al., *Impaired anabolic response of muscle protein synthesis is associated with S6K1 dysregulation in elderly humans.* FASEB J, 2004. 18(13): p. 1586-7.
6. Bouillon, R., et al., *Vitamin D deficiency.* N Engl J Med, 2007. 357(19): p. 1980-1; author reply 1981-2.
7. Lips, P., *Vitamin D status and nutrition in Europe and Asia.* J Steroid Biochem Mol Biol, 2007. 103(3-5): p. 620-5.
8. Wicherts, I. S., et al., *Vitamin D status predicts physical performance and its decline in older persons.* J Clin Endocrinol Metab, 2007. 92(6): p. 2058-65.
9. Zittermann, A., *Molecular Nutrition & Food Research, "The estimated benefits of vitamin D for Germany"* Published online ahead of print, doi: 10.1002/mnfr.200900494.
10. Pfeifer, M., et al. Review: *Vitamin D and muscle function,* Osteoporos Int. 2002 March; 13(3):187-94.
11. Visser, M., et al. *Low Vitamin D and High Parathyroid Hormone Levels as Determinants of Loss of Muscle Strength and Muscle Mass (Sarcopenia): The Longitudinal Aging Study Amsterdam,* The Journal of Clinical Endocrinology & Metabolism, 2003, 8(12):5766-5772.
12. Bendahan D, Maffei J P, Ghattas B, Confort-Gouny S, Le Guern M E, Cozzone P J.
Citrulline/malate promotes aerobic energy production in human exercising muscle. Br J Sports Med. 2002 August; 36(4):282-9.
13. Pérez-Guisado J, Jakeman P M. Citrulline malate enhances athletic anaerobic performance and relieves muscle soreness. J Strength Cond Res. 2010 May; 24(5): 1215-22.
14. WHO, Keep fit for life: meeting the nutritional needs of older persons. 2002. 15. Holick, M. F., *Vitamin D deficiency.* N Engl J Med, 2007. 357(3): p. 266-81.
16. Lesser, S., et al., *Nutritional situation of the elderly in Eastern/Baltic and Central/Western Europe—the Ageing Nutrition project.* Ann Nutr Metab, 2008. 52 Suppl 1: p. 62-71.
17. Raats, M. L., L. de Groot, and W. van Staveren, *Food for the ageing population.* 2009, Cambridge, England: Woodhead Publishing Limited.
18. Bartali, B., et al., *Low nutrient intake is an essential component of frailty in older persons.* J Gerontol A Biol Sci Med Sci, 2006. 61(6): p. 589-93.
19. Semba, R. D., et al., *Low serum micronutrient concentrations predict frailty among older women living in the community.* J Gerontol A Biol Sci Med Sci, 2006. 61(6): p. 594-9.
20. Marzani, B., et al., *Antioxidant supplementation restores defective leucine stimulation of protein synthesis in skeletal muscle from old rats.* J Nutr, 2008. 138(11): p. 2205-11.
21. Seshadri, S., et al., *Plasma homocysteine as a risk factor for dementia and Alzheimer's disease.* N Engl J Med, 2002. 346(7): p. 476-83.

The invention claimed is:

1. A method for treating a loss of any one of muscle mass, muscle strength and muscle function, or any combination thereof, in an adult mammal, comprising administering to an adult mammal with loss in muscle mass, muscle strength and/or muscle function a nutritional composition providing,:
   (i) about 1-2 g leucine, wherein the composition is administered as 1 to 2 servings daily, of which about 20-50 weight % is in a free form, relative to the total amount of leucine; and
   (ii) 20 to 75 µg of vitamin D per day.

2. The method according to claim 1, wherein said method involves administering the nutritional composition providing said daily dosage in 1 to 2 servings daily, each serving comprising between 80 and 200 kcal.

3. The method according to claim 1, wherein the nutritional composition providing said daily dosage has a caloric value of less than about 500 kcal per 100 g of dry weight.

4. The method according to claim 1, wherein the nutritional composition providing said daily dosage has an amount of leucine of at least about 5 g leucine per 100 g of dry weight of which at least about 20 weight % is in a free form, relative to the total leucine.

5. The method according to claim 1, wherein the nutritional composition providing said daily dosage comprises at least about 11 wt % leucine, based on proteinaceous matter.

6. The method according to claim 1, wherein the nutritional composition providing said daily dosage further comprises a source of fat and a source of digestible carbohydrates.

7. The method according to claim 1, wherein the nutritional composition providing said daily dosage has an amount of proteinaceous matter of at least about 12 g per 100 kcal.

8. The method according to claim 7, wherein said proteinaceous matter comprises at least about 80 weight % of whey protein.

9. The method according to claim 1, wherein the nutritional composition providing said daily dosage is a low-caloric composition, the energy of which does not exceed 100 kcal/ml.

10. The method according to claim 1, said adult mammal following a weight loss program, an energy restriction program and/or an exercise program.

11. The method according to claim 1, wherein said adult mammal suffers from overweight or obesity.

12. The method according to claim 1, wherein the adult suffers from a disorder or symptom selected from the group consisting of sarcopenia, insufficient muscle protein synthesis, muscle degradation, muscle proteolysis, muscle atrophy, muscle dystrophy, muscle catabolism, muscle wasting and loss of muscle strength.

13. The method according to claim 1, wherein said adult mammal suffers from sarcopenia.

* * * * *

UNITED STATES PATENT AND TRADEMARK OFFICE
CERTIFICATE OF CORRECTION

| | |
|---|---|
| PATENT NO. | : 10,045,999 B2 |
| APPLICATION NO. | : 14/750061 |
| DATED | : August 14, 2018 |
| INVENTOR(S) | : Jourdan et al. |

It is certified that error appears in the above-identified patent and that said Letters Patent is hereby corrected as shown below:

In the Claims

Column 22, Line 10, Claim 1 Should read:
1. A method for treating a loss of any one of muscle mass, muscle strength and muscle function, or any combination thereof, in an adult mammal, comprising administering to an adult mammal with loss in muscle mass, muscle strength and/or muscle function a nutritional composition providing,:
(i) about 1-2 g leucine per 100 mL, wherein the composition is administered as 1 to 2 servings daily, of which about 20-50 weight % is in a free form, relative to the total amount of leucine; and
(ii) 20 to 75 µg of vitamin D per day.

Signed and Sealed this
Eighteenth Day of June, 2024

Katherine Kelly Vidal
*Director of the United States Patent and Trademark Office*